(12) United States Patent
Abbott et al.

(10) Patent No.: US 8,830,648 B2
(45) Date of Patent: Sep. 9, 2014

(54) MAGNETIC MANIPULATION AND NAVIGATION SYSTEM FOR A MAGNETIC ELEMENT

(75) Inventors: Jake J. Abbott, Salt Lake City, UT (US); Bradley Kratochvil, Zurich (CH); Michael P. Kummer, Zurich (CH); Bradley Nelson, Zumikon (CH)

(73) Assignee: ETH Zurich, Zurich (CH)

(*) Notice: Subject to any disclaimer, the term of this patent is extended or adjusted under 35 U.S.C. 154(b) by 191 days.

(21) Appl. No.: 13/395,577

(22) PCT Filed: Sep. 9, 2010

(86) PCT No.: PCT/EP2010/005533
§ 371 (c)(1), (2), (4) Date: Jul. 20, 2012

(87) PCT Pub. No.: WO2011/029592
PCT Pub. Date: Mar. 17, 2011

(65) Prior Publication Data
US 2012/0281330 A1    Nov. 8, 2012

(30) Foreign Application Priority Data

Sep. 11, 2009 (EP) .................................. 09011664
Nov. 2, 2009 (EP) .................................. 09013746

(51) Int. Cl.
*H01H 47/00* (2006.01)
*A61B 19/00* (2006.01)
*A61F 9/007* (2006.01)
*A61B 17/00* (2006.01)

(52) U.S. Cl.
CPC ......... *A61B 19/22* (2013.01); *A61B 2019/2253* (2013.01); *A61F 9/007* (2013.01); *A61B 2019/5238* (2013.01); *A61B 2019/5265* (2013.01); *A61B 2019/5227* (2013.01); *A61B 2017/00876* (2013.01)
USPC .......................................... 361/139; 361/143

(58) Field of Classification Search
USPC ........................................ 361/139, 143, 160
See application file for complete search history.

(56) References Cited

U.S. PATENT DOCUMENTS 5,654,864 A     8/1997  Ritter et al.
6,128,174 A  * 10/2000  Ritter et al. ................... 361/143
(Continued)

FOREIGN PATENT DOCUMENTS

WO        0054690  A1    9/2000
WO     2006137877  A2   12/2006

OTHER PUBLICATIONS

Abbott, Jake J. et al., "Modeling Magnetic Torque and Force for Controlled Manipulation of Soft-Magnetic Bodies" IEEE Transactions on Robotics, Dec. 2007, pp. 1247-1252, vol. 23, No. 6.

(Continued)

*Primary Examiner* — Danny Nguyen
(74) *Attorney, Agent, or Firm* — The Webb Law Firm (57) ABSTRACT

A magnetic manipulation and navigation system for moving a magnetic element through a body comprising at least six electromagnets fixed in relation to said body and a control unit supplying the current for the electromagnets. The electromagnets have soft magnetic cores and the current supplied by the control unit to each of the electromagnets is adapted to operate the electromagnetic coils of each of the electromagnets in their core's linear regions being delimited by the value of the flux density of each electromagnet being in an interval between the negative and positive saturation value of each electromagnet, the lower representation showing the deviation due to the use of soft magnetic cores in all electromagnets.

18 Claims, 10 Drawing Sheets

(56) References Cited

U.S. PATENT DOCUMENTS

| | | | |
|---|---|---|---|
| 6,311,082 B1 | 10/2001 | Creighton, IV et al. | |
| 7,699,768 B2* | 4/2010 | Kishawi et al. | 600/9 |
| 2004/0138552 A1 | 7/2004 | Harel et al. | |
| 2007/0088197 A1 | 4/2007 | Garibaldi et al. | |
| 2007/0264898 A1* | 11/2007 | Imura | 445/23 |

OTHER PUBLICATIONS

Gillies, G.T. et al., "Magnetic manipulation instrumentation for medical physics research", Review of Scientific Instruments, Mar. 1994, pp. 533-562, vol. 65, No. 3.

Nagy, Zoltan et al., "Modeling Assembled—MEMS Microbots for Wireless Magnetic Control" IEEE International Conference on Robotics and Automation, May 19-23, 2008, pp. 874-879.

Yesin, Kemal Berk et al., "Analysis and Design of Wireless Magnetically Guided Microbots in Body Fluids", Proceedings of the 2004 IEEE International Conference on Robotics and Automation, Apr. 2004, pp. 1333-1338.

Yesin, K. Berk et al., "Modeling and Control of Untethered Biomicrorobots in a Fluidic Environment Using Electromagnetic Fields", The International Journal of Robotics Research, 2006, pp. 527-536, vol. 25.

* cited by examiner

MAGNETIC MANIPULATION AND NAVIGATION SYSTEM FOR A MAGNETIC ELEMENT

TECHNICAL FIELD

The present invention relates to a magnetic manipulation and navigation system for moving a magnetic element through a body comprising at least six electromagnets arranged in a predetermined position to said body. Such a body usually is a cavity comprising a liquid or soft tissue and a magnetic element to be displaced inside said cavity.

PRIOR ART

U.S. Pat. No. 6,311,082 discloses a magnetic manipulation system comprising a number of at least six fixed or manually movable magnets, preferably fixed electromagnets or movable permanent magnets. The document raises the issue that large fixed electromagnets will hamper the use of these elements in connection with an imaging system.

WO 00/54690 relates to a magnetic manipulation system. Said document states that positioning of superconductive electromagnets is difficult when they are employed as stationary coils to guide magnetic elements. WO 00/54690 uses gapped toroid magnets allowing moving a magnetic element within a body by translating the magnets relative to said body. Said magnets are preferably permanent magnets connected by a flux return path. It is also disclosed that the magnets can be electromagnets.

WO 2006/137877 relates to a magnetic manipulation and navigation system for moving a magnetic element through a body using permanent magnets and provides a unit to accurately control the position and orientation of said permanent magnets. Said document mentions that the use of permanent magnets is superior to the use of superconducting magnets comprising superconducting electromagnetic coils.

US 2007/088197 relates to a magnetic navigation system for moving catheters as a magnetic element through a body. The system uses electromagnetic source magnets which might be superconducting or not. The magnetic field is changed by changing the current supplied to the source magnets. The magnetic navigation system according to US 2007/088197 uses a magnetic element having a changeable magnetic moment, i.e. an electromagnet.

A further device for navigating and manoeuvring of an in vivo vehicle by extracorporeal devices is known from US 2004/0138552. Electronic detection elements are used to detect the position of such a vehicle, while a control unit modulates the strength and direction of an electromagnetic field vector provided at the space of the vehicle. It is mentioned that the electromagnets may have soft magnetic cores.

The prior art states that electromagnets are difficult to use for such manipulation system, since they have space requirements which usually conflict with the cavity, space or body within which said magnetic element is to be displaced. Additionally such magnets may block the beam path of an imaging system used to follow the movement of the magnetic element.

SUMMARY OF THE INVENTION

Based on said prior art it is an object of the invention to provide a magnetic manipulation and navigation system for moving a magnetic element through a body which allows a more precise control of the movement with a simple control and especially avoiding use of superconducting electromagnets. This can be achieved by using at least six electromagnets having soft magnetic cores, said magnets being fixed in relation to said body, and the control unit supplying the current for the electromagnets, wherein the current is adapted to operate the electromagnetic coils in their core's linear regions.

The important feature of using the core's linear regions consists of the fact that the control unit provides signals to the different, e.g. six or eight, electromagnets having soft magnetic cores, wherein no one of the magnets is working in a saturation regime. This means that each magnet is still in the regime, where the magnetization of the core increases at a ferromagnetic rate and not a paramagnetic rate, i.e. the magnet is not in saturation regime.

The linear region of each core is thus delimited by the fact that each magnetic core is not in saturation. Saturation can be defined through the fact that the magnetization curve levels off. Until then the relationship of magnetization to applied field remains linear—in the interval around 0 Ampere—and works in the ferromagnetic regime, before the saturation would be reached and the increase switch to the paramagnetic rate.

A magnetic manipulation and navigation system for moving a magnetic element through a body comprises at least six electromagnets fixed in relation to said body and a control unit supplying the current for the electromagnets, wherein the electromagnets have soft magnetic cores, being characterized in that the current supplied by the control unit to each of the electromagnets is adapted to operate the electromagnetic coils of each of the electromagnets in an linear region of the cores being delimited by the value of the flux density of each electromagnet being in an interval between the negative and positive saturation value of each electromagnet.

The invention is based on the insight, that the precise control of the magnetic element to be displaced in said body space can be achieved when the coils of the electromagnets are controlled in their core's linear regions, i.e. that any change of the strength of the current of any one electromagnetic coil translates into a change of the vector value of the magnetic field according to a linear function of said current and that the change of several currents thus permits to perfect orientation and displacement of the magnetic element within the body.

Although the different currents of the different electromagnetic coils influence the magnetic field of the other magnets, each current is controlled that each magnet remains in the linear region outside the saturation regime.

The invention proposes a system and method for applying forces to a soft or permanent magnetic body using a set of electromagnetic coils with soft magnetic cores.

The system consists of a series of six or more electromagnetic coils, each having a ferromagnetic core. The control unit supplying the current for the coils is adapted to provide currents to the coils that they are operated in their core's linear regions, which allows exploiting the linear superposition of the magnetic field generated by the different coils to generate a field orientation and gradient within the workspace. As opposed to air-core electromagnets according to prior art devices, where the interaction between coils is minimal and can often be neglected, the addition of ferromagnetic cores to the electromagnetic coils according to the invention and their positions in space is explicitly taken into account by the control unit when determining the amount of current to supply to each coil.

The system can apply forces, due to gradients in the magnetic field, and torques, due to the magnetic field alignment on an arbitrary ferromagnetic body within the workspace. This system allows up to five degrees-of-freedom control, three degrees for applying force and two degrees for orienting
} torques. The electromagnetic coils can be located arbitrarily around the workspace depending on the desired performance of forces and torques exerted on the manipulated object, and the method's explicit control of both the magnetic field's orientation and gradient enables the system to both push and pull on the target body without having to completely surround the workspace.

The system can be controlled manually by an operator using visual or other position feedback in a force controlled paradigm. It is also possible to use a computer system that uses visual or other position feedback for closed-loop positioning control.

The magnetic element, also called microrobot, can move through a large workspace, and is completely unrestrained in the rotation degrees of freedom, which is not known in prior art. This level of wireless control is achieved with a novel electromagnetic system. Whereas magnetic manipulation has typically relied on uniform-field and/or orthogonal systems, which are simple in terms of modelling and control, the present system uses complex nonuniform magnetic fields. The embodiment shown is designed for the control of intraocular microrobots for delicate retinal procedures, but can also be used in other medical applications or micromanipulation under an optical microscope.

It is noted that although the specific embodiment shown relates to the use of the device in connection with a magnetic element to be manipulated in a body being a human and wherein the space within which the magnetic element is positioned is a liquid, it is also contemplated that the body within which the magnetic element is positioned is a body in an industrial environment. Furthermore, the body may comprise a fluid, especially a gas or a liquid for the floating positioning of the magnetic element.

The invention is further directed to a method to an improved control of the magnetic field at a specific point in space, wherein the wording point in space also relates to a small volume around a given point. Of course, all prior art documents control in some way the value of the magnetic field at a specific point, but the control of the currents in the non-saturation mode of the different coils allows for a more specific and precise control.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
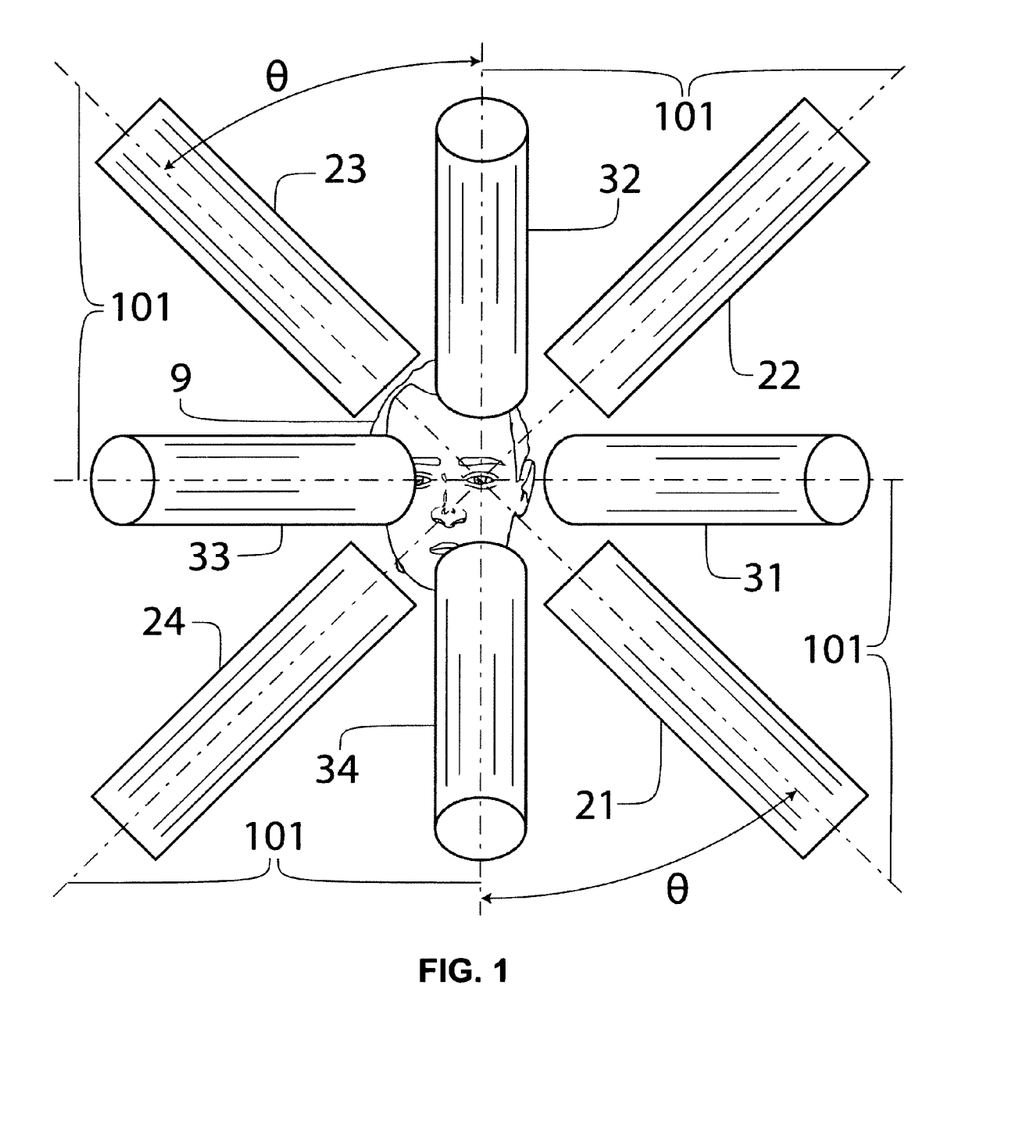
FIG. 1 shows a schematic view from above on the magnets of a system according to the invention.

FIG. 1 shows a schematic view from above on the magnets of a system according to the invention. The system according to the embodiment is arranged for moving a magnetic element (not shown) within an eye. The eye of a person constitutes the body 9 within which the element is to be positioned and displaced. The eye comprises and is a cavity comprising a liquid, constituting the workspace, denoted with the reference numeral 3 in FIG. 3.

The embodiment according to FIG. 1 specifically comprises eight electromagnets fixed in relation to said body. Usually the electromagnets are attached to a fixed frame and the patient, i.e. the body is positioned in relationship to this frame. It might therefore be possible to move the patient during a procedure. Within one embodiment the system has a fixed position with respect to the body whenever the system is in use. Within a different embodiment, the volume containing the magnetic element can be moved without any displacement of the magnetic element, if the system is turned on during the movement. Therefore the electromagnets are arranged in a predetermined position to said body; this may be a fix relationship or there can be a controlled and thus predetermined movement.

There are four electromagnets 21, 22, 23 and 24 being arranged in the drawing plane of FIG. 1, i.e. arranged around the head 9 of a person. The longitudinal axis 101 of the electromagnets 21, 22, 23, 24 intersect at one single point 102, shown in FIG. 2. Said intersection point 102 is in the vicinity of the cavity within which a magnetic element has to be positioned and displaced. In the representation of FIG. 1 this cavity is the eye of a person and therefore the intersection point 102 is near this eye.

Beside the four electromagnets 21, 22, 23 and 24 in the drawing plane of FIG. 1 there are additional four electromagnets 31, 32, 33 and 34 being oriented in an angle of 45 degree in view of the plane of the four electromagnets 21, 22, 23 and 24. The additional four electromagnets 31, 32, 33 and 34 each have a longitudinal axis 101 and the position of the four electromagnets 31, 32, 33 and 34 is such that their longitudinal axis 101 cross the drawing plane of FIG. 1 at the intersection point 102. In other words, all eight electromagnets 21 to 24 and 31 to 34 are oriented towards the intersection point 102. Although the embodiment shown in FIG. 1 uses eight electromagnets, within another embodiment not shown in the drawings, it is possible to obtain the precise orientation of a magnetic element and its displacement within the cavity using six magnets.

All electromagnets 21 to 24 and 31 to 34 comprise a rod having said axis 101 as symmetry axis and is surrounded by a coil. The electromagnets 21 to 24 are also called the lower set while the electromagnets 31 to 34 above the plane of magnets 21 to 24 are called the upper set.

Figure 2:
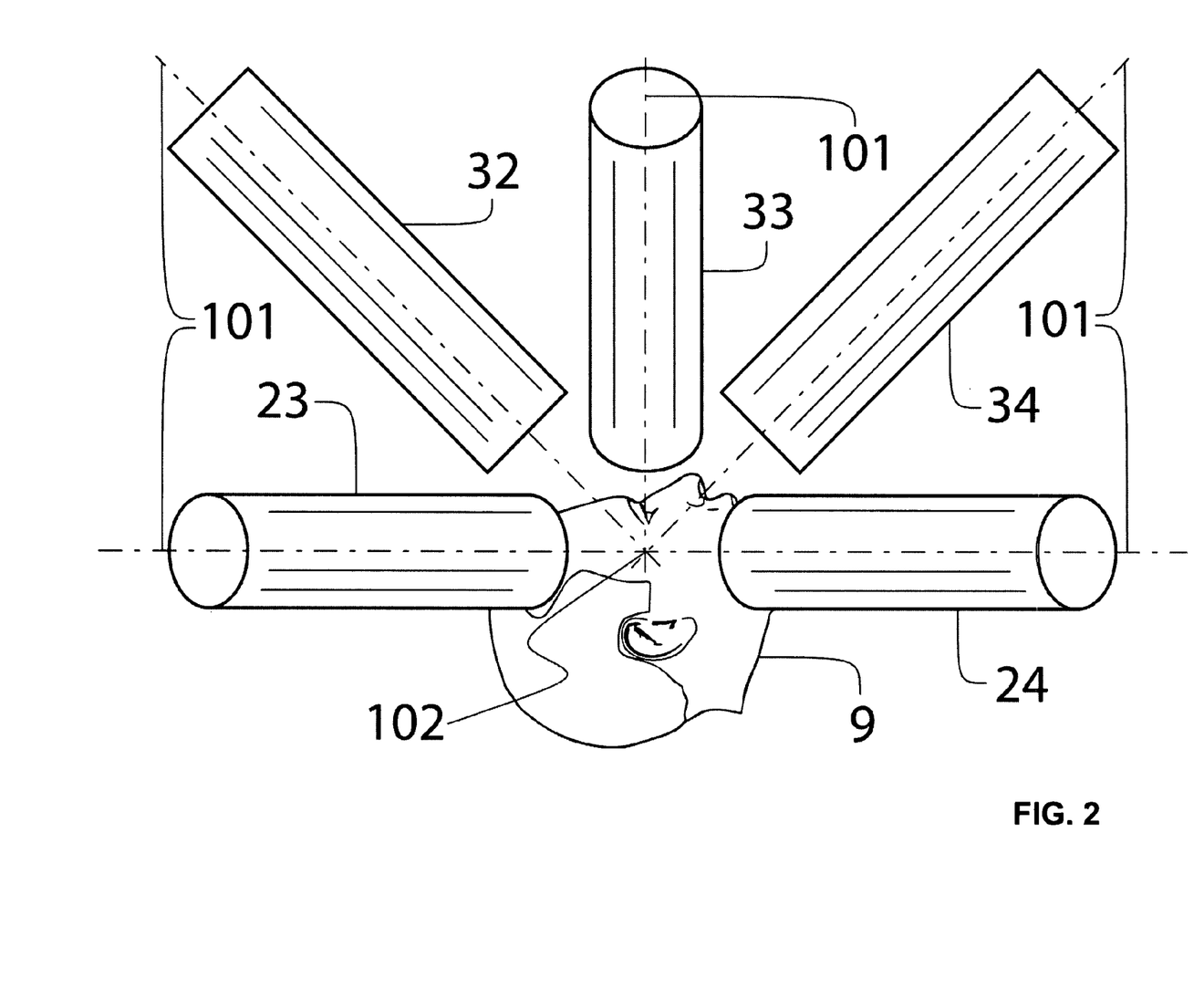
FIG. 2 shows a schematic side-view on the magnets of the system according to FIG. 1.

FIG. 2 shows a schematic side-view on the electromagnets of the system according to FIG. 1. Only electromagnets 23 and 24 are visible from the group of horizontally oriented magnets. Three electromagnets 32, 33 and 34 are visible from the group of inclined oriented magnets, wherein electromagnets 32 and 34 are in the drawing plane.

Figure 3:
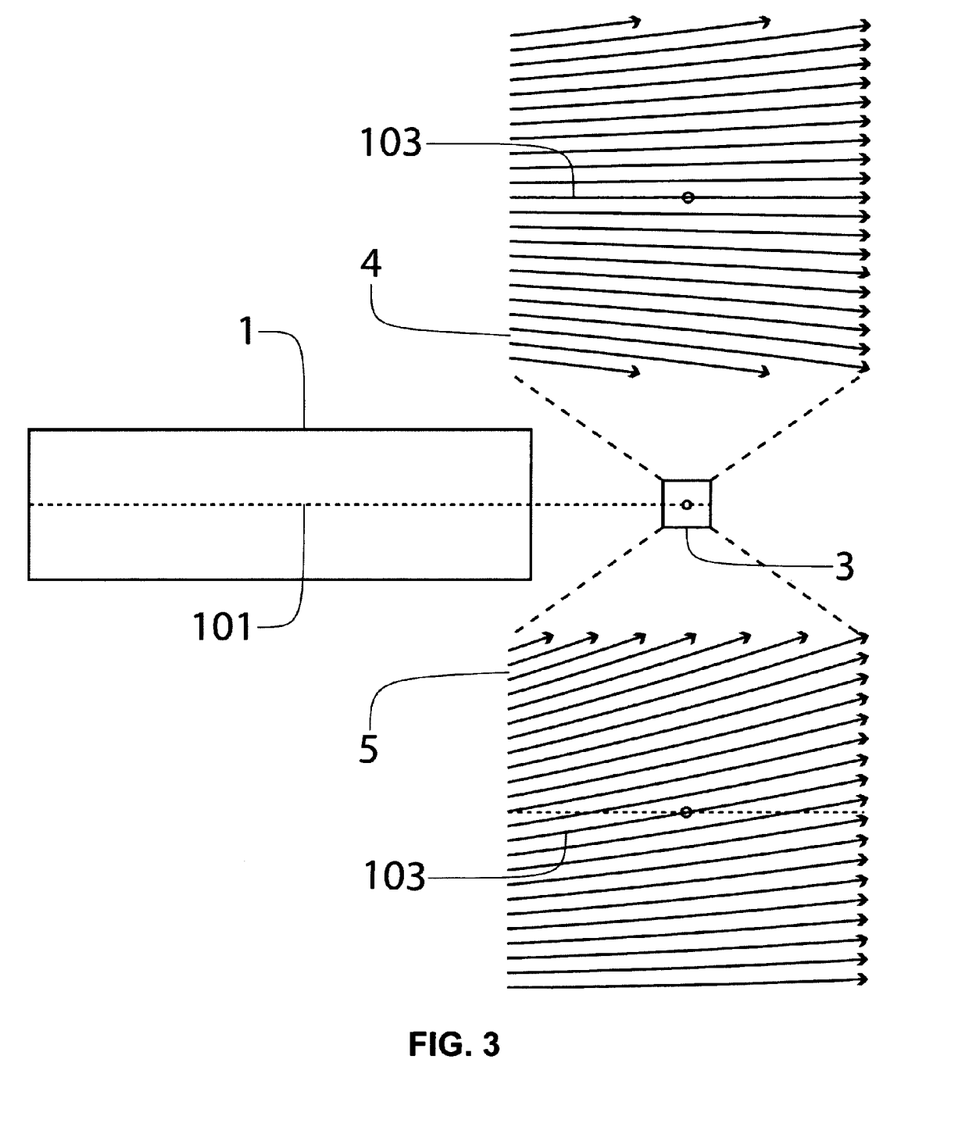
FIGS. 3 & 4 show a representation of the magnetic field of a single soft-magnetic-core electromagnet with and without any neighbouring electromagnets.
Figure 4:
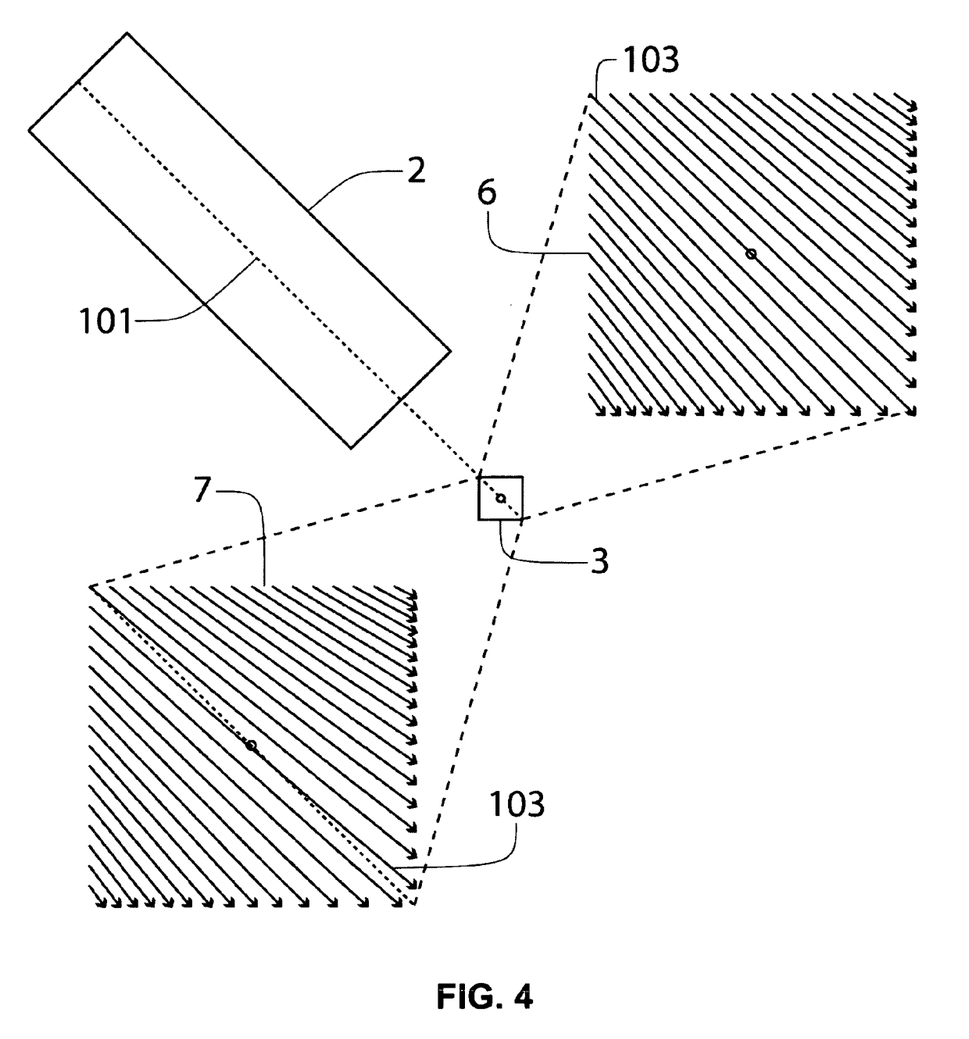

FIGS. 3 and 4 show a representation of the magnetic field of a single soft-magnetic-core electromagnet 1 with and without the influence of any neighbouring electromagnets. Said electromagnet 1 can be any of the electromagnets 21 to 24 and 31 to 34 of the embodiment according to FIG. 1 and the representation of FIGS. 3 and 4 is equally applicable in a situation of a different number of electromagnets. The use of soft-magnetic-core electromagnets allows fields that are approximately 20 times stronger over air cores. Air cores would have the advantage that their fields are independent.

FIG. 3 shows an electromagnet 1 with no angular offset with respect to a horizontal reference plane, i.e. the drawing plane of FIG. 3. Electromagnet 1 can therefore be any of magnets 21 to 24. A vertical cross section of the workspace of the system is denoted by the small square 3. The longitudinal axis of the electromagnet 1 intersects the workspace 3. The upper representation 4 of field lines shows the field of a single soft-magnetic-core electromagnet without any neighbouring electromagnets (ex situ). Representation 4 shows the field lines in the plane of FIG. 3. It is not necessary to show the effect on the field outside the drawing plane, since looking from the face of the electromagnet along its centreline 101 always leads to a symmetry left and right as far as neighbouring cores are concerned. It's in the vertical plane, that the field gets deflected due to the surrounding electromagnets. The field lines do not deflect and the central field line 103 perfectly aligns with the symmetry axis 101 of the electromagnet 1. In contrast the field due to a single soft-magnetic-core electromagnet in the system (in situ), surrounded by its seven neighbours, can be seen in the lower representation 5. The field lines do not exhibit an axisymmetric pattern anymore since the current running through said electromagnet 1 induces a field in the surrounding soft-magnetic cores resulting in deviating field contributions.

Therefore any current supplied to any one of the electromagnets, e.g. 21, induces a magnetic field in the soft-magnetic core of all surrounding electromagnets, e.g. 22 to 24 and 31 to 34, resulting in deviating field contributions and destroying the symmetry between the central field line 103 and the symmetry axis 101 of the electromagnet receiving the current.

The same effect can be observed for an electromagnet 2 with angular offset with respect to a horizontal reference plane (see FIG. 4). Electromagnet 2 can therefore be any of magnets 31 to 34. The drawing plane of FIG. 4 comprises the longitudinal axis 101 of said electromagnet 2. The longitudinal axis of the electromagnet 2 intersects the workspace 3. The upper representation 6 of field lines shows the field of the single soft-magnetic-core electromagnet 2 without any neighbouring electromagnets (ex situ). The central field line 103 along the symmetry axis of 2 ex situ again shows no field contribution deviating from the symmetry axis 101. The contrary is the case for 2 in situ according to the lower representation. The field lines are influenced by the surrounding soft-magnetic-core electromagnets.

The typical workspace 3 of a prototype constructed in accordance with the invention was a 25 mm diameter sphere, although depending on the magnets chosen different workspaces 3 would be possible, and the representation in FIGS. 3 and 4 show a cylinder. The body 9 of the prototype had a 130 mm diameter sphere as open volume between the electromagnets 21, 22, 23 and 24 to allow accommodating e.g. a head of a small animal. The workspace 3 is isotropic with an ability to generate magnetic forces in any direction and any magnetic element pose, e.g. comprising the possibility to levitate the magnetic element against its own weight as well as to provide downward and lateral forces. The workspace 3 can be filled with any fluid, e.g. a liquid or a gas, wherein the magnetic properties of the device are chosen to maintain a magnetic element floating in that workspace.

Each electromagnet 21 to 24 and 31 to 34 comprises a soft magnetic core; especially a rod of a high-permeability material used to concentrate the magnetic field. Someone skilled in the art can choose such from a wide variety of high-permeability materials which are often ferromagnetic or ferrimagnetic. He can e.g. choose a so called soft magnetic material such as a Fe-50% Co alloy, Permalloy (Ni—Fe), soft iron, iron-silicon alloys, or stainless steel.

The system is capable of performing control of both soft and permanent magnetic bodies. In the case of a hard magnetic body, the magnetic moment is rigidly connected to the frame of the body. With a soft-magnetic body, the magnetic moment is dependent on the applied field and not rigidly connected to the body.

Figure 9:
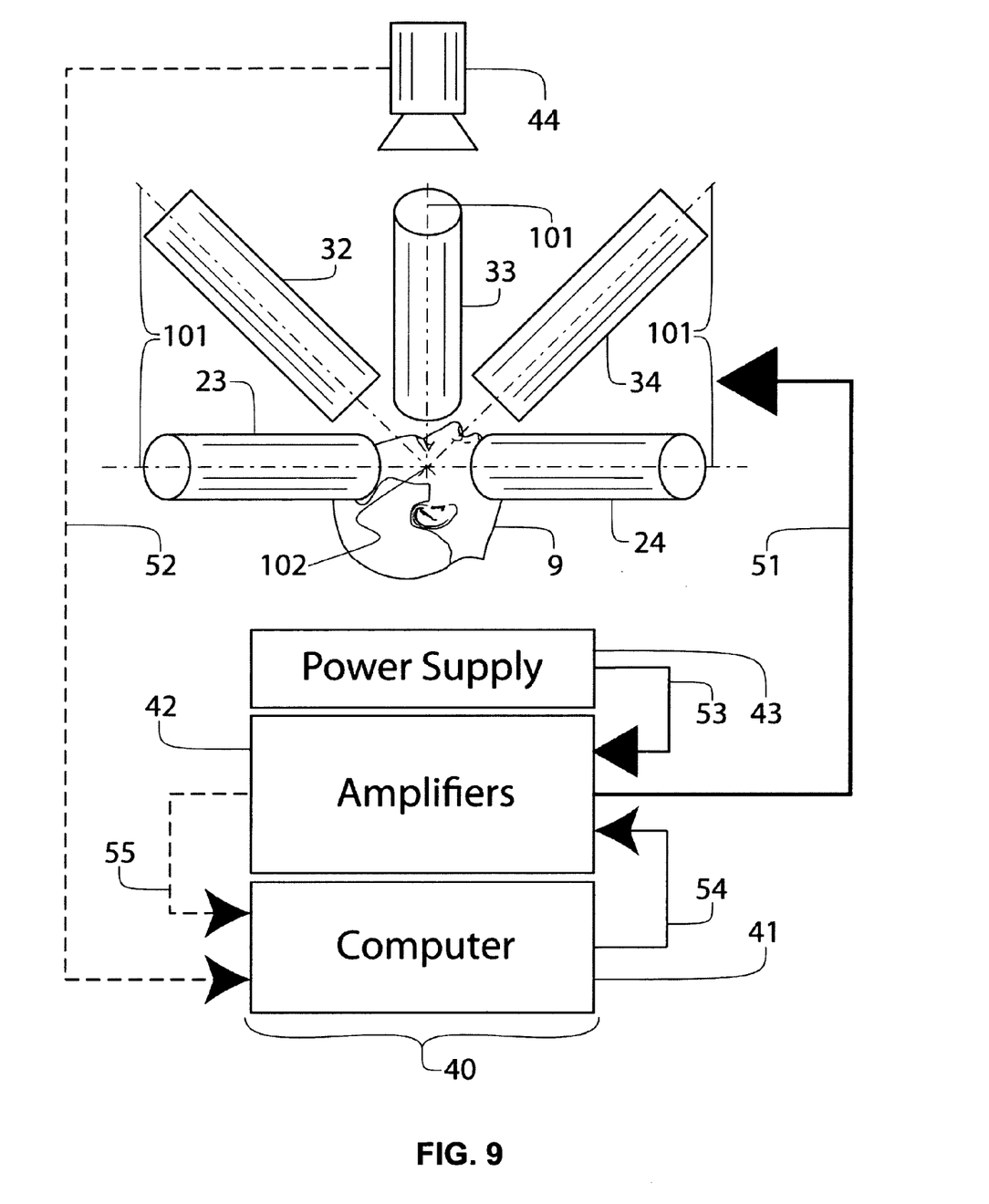
FIG. 9 shows a schematic side-view on the system according to FIG. 1 including a control unit.

Within a given static arrangement of electromagnets, each electromagnet creates a magnetic field throughout the workspace. In the case of air-core electromagnets the field contributions of the individual electromagnets can be computed individually and linearly superimposed to determine the field at a location in the workspace. When the electromagnets have soft-magnetic cores, the field contributions of the individual electromagnets are no longer decoupled. Current flowing in one electromagnet also induces a magnetic field in its neighbouring cores as depicted in FIGS. 3 and 4 as this system uses soft-magnetic-core electromagnets 21 to 24 and 31 to 34. To account for the magnetic field induced in neighbouring electromagnets, the field contribution of a given electromagnet is calculated in situ. This calculation can be derived from a variety of methods such as measuring the field generated by a reference current through an individual coil throughout the workspace and interpolating the field at a desired location, through the use of finite element analysis of the system, mathematically modelling the various cores and their interactions, or other methods familiar to one versed in the state-of-the-art. Someone skilled in the art can choose different implementations of the current control schemes in the control unit 40 as seen in FIG. 9. The common point is that the control unit 40 is to be adapted to operate the electromagnetic coils of each of the electromagnets 21-24 and 31-34 in their core's linear regions.

The cores are chosen with minimal hysteresis (the cores coercivity $H_c$ should be less than 1000 A/m preferably less than 300 A/m) and the system is operated in the cores' linear magnetization region, which enables the control unit to implement the assumption that the field contributions of the individual currents superimpose linearly. The control unit calculates the desired current through each of the coils by building a linear set of equations dependent on current that describe the torque and force, or alternately the field orientation and force, on the modelled soft or hard-magnetic body. Using linear algebra, the current through each coil is able to be found by techniques such as the pseudoinverse or similar mathematical tools. Depending on the availability of closed-loop feedback, the field can either be calculated at the location of the magnetic body to be controlled, or if the magnetic field does not vary greatly across the workspace, it may be calculated at the centre of the workspace.

The following proposal of a controller starts from the assumption that the magnetic element to be controlled is a magnetized body described by a magnetic moment M in units A·m². With a permanent magnet, the magnetic moment M is assumed to have a constant magnitude and be rigidly connected to the frame of the body. With a soft-magnetic body, the magnetic moment is dependent on the applied field and cannot be assumed to be rigidly attached to the body. That is, the magnetic moment can rotate with respect to the body and its magnitude can vary greatly with changes in the applied field. In prior work, accurate models for the field-dependent magnetic moment of axially symmetric bodies as shown by J. J. Abbott et al. in "Modeling Magnetic Torque and Force for controlled manipulation of soft-magnetic bodies" were generated. These models include ellipsoids and spheres, as well as assembled-MEMS structures like those used in the present embodiments, for which the modeling was presented by Nagy et al. in "Modeling Assembled-MEMS Microrobots for wireless magnetic control".

The torque on the magnet, in units N·m, is expressed as:

$$T = M \times B \qquad (1)$$

where B is the value of the applied magnetic field's flux density at the location of M in units T. It can be found for example in "Permanent Magnet and Electromechanical Devices" by E. P. Furlani. The torque tends to align the magnetic moment with the applied field. In the case of soft-magnetic bodies, the torque tends to align the longest axis of the body (referred to as the easy axis) with the field. It is impossible to apply torque about the axis of M, which is the reason why the goal of the present application is to achieve 5-DOF control rather than 6-DOF control. In soft-magnetic bodies, this means that rotations about the long axis of the body cannot be performed. The skew-symmetric matrix form of a vector to represent vector cross products, $M \times B = Sk(M)B$ is used, where $$Sk(M) = Sk\left(\begin{bmatrix} m_x \\ m_y \\ m_z \end{bmatrix}\right) = \begin{bmatrix} 0 & -m_z & m_y \\ m_z & 0 & -m_x \\ -m_y & m_x & 0 \end{bmatrix} \qquad (2)$$

where x, y, and z explicitly refer to the basis directions of the world frame in which all vectors are expressed. The force on the magnetic moment, in units N, is expressed as $$F = (M \cdot \nabla)B \qquad (3)$$

Since there is no electric current flowing through the region occupied by the body, Maxwell's equations provide the constraint $\nabla \times B = 0$. This allows expressing (3), after some manipulation, in a more intuitive form:

$$F = \begin{bmatrix} \frac{\partial B}{\partial x} & \frac{\partial B}{\partial y} & \frac{\partial B}{\partial z} \end{bmatrix}^T M \qquad (4)$$

Note that the applied magnetic field as H in units A/m can be described with $B = \mu_0 H$ and $\mu_0 = 4\pi 10^{-7}$ T·m/A.

Within a given static arrangement of electromagnets, each electromagnet creates a magnetic field throughout the workspace that can be precomputed. At any given point in the workspace P, the magnetic field due to a given electromagnet can be expressed by the vector $B_e(P)$, whose magnitude varies linearly with the current through the electromagnet, and as such can be described as a unit-current vector in units T/A multiplied by a scalar current value in units A:

$$B_e(P) = \tilde{B}_e(P) i_e \qquad (5)$$

The subscript e represents the contribution due to the $e^{th}$ electromagnet. The field $B_e(P)$ is the field due to the current flowing through electromagnet e and due to the soft-magnetic cores of every electromagnet. With air-core electromagnets, the individual field contributions are decoupled, and the fields can be individually precomputed and then linearly superimposed. This is not the case with soft-magnetic-core electromagnets; so that the field contributions of a given electromagnet are to be precomputed in situ. However, if an ideal soft-magnetic material with negligible hysteresis is assumed, and the system operates with the cores in their linear magnetization region, and it can still be assumed that the field contributions of the individual currents (each of which affect the magnetization of every core) superimpose linearly. Thus, it is assumed that the magnetic field at a point in the workspace is simply the sum of the contributions of the individual currents:

$$B(P) = \sum_{e=1}^{n} B_e(P) = \sum_{e=1}^{n} \tilde{B}_e(P) i_e \qquad (6)$$

This assumption is clearly also valid for air-core electromagnets. This linear summation of fields can be expressed as:

$$B(P) = \begin{bmatrix} \tilde{B}_1(P) & \cdots & \tilde{B}_n(P) \end{bmatrix} \begin{bmatrix} i_1 \\ \vdots \\ i_n \end{bmatrix} = \lfloor B(P) \rfloor I \qquad (7)$$

The $3 \times n \lfloor B(P) \rfloor$ matrix is known at each point in the workspace and can be calculated online, or calculated offline and then interpolated. It is also possible to express the derivative of the field in a given direction in a specific frame, for example the x direction, as the contributions from each of the currents:

$$\frac{\partial B(P)}{\partial x} = \begin{bmatrix} \frac{\partial \tilde{B}_1(P)}{\partial x} & \cdots & \frac{\partial \tilde{B}_n(P)}{\partial x} \end{bmatrix} \begin{bmatrix} i_1 \\ \vdots \\ i_n \end{bmatrix} = \lfloor B_x(P) \rfloor I \qquad (8)$$

Considering (1) and (4), the magnetic torque and force on the microrobot (i.e. the magnetic element) can be expressed as $$\begin{bmatrix} T \\ F \end{bmatrix} = \begin{bmatrix} Sk(M)\lfloor B(P) \rfloor \\ M^T \lfloor B_x(P) \rfloor \\ M^T \lfloor B_y(P) \rfloor \\ M^T \lfloor B_z(P) \rfloor \end{bmatrix} \begin{bmatrix} i_1 \\ \vdots \\ i_n \end{bmatrix} = \lfloor A_{T,F}(M, P) \rfloor I \qquad (9)$$

That is, for each microrobot pose, the n electromagnet currents are mapped to a torque and force through a 6×n actuation matrix $\lfloor A_{T,F}(M,P) \rfloor$. For a desired torque/force vector, the choice of currents that gets us closest to the desired torque/force value can be found using the pseudoinverse presented by R. A. Horn et al. in "Matrix Analysis":

$$I = \lfloor A_{T,F}(M, P) \rfloor^{-1} \begin{bmatrix} T_{des} \\ F_{des} \end{bmatrix} \qquad (10)$$

N.B.: The use of (9) requires knowledge of the microrobot's pose and magnetic moment. If there are multiple solutions to achieve the desired torque/force, the pseudoinverse finds the solution that minimizes the 2-norm of the current vector, which is desirable for the minimization of both energy consumption and heat generation. The pseudoinverse of $\lfloor A \rfloor$ makes use of the singular value decomposition $\lfloor A \rfloor = U\Sigma V^T$, where $\Sigma$ is the 6×n singular-value matrix, where the left-most 6×6 elements form a diagonal matrix of the six ordered singular values $\sigma_j$, U is the 6×6 orthonormal matrix whose columns are the six output singular vectors, and V is the n×n orthonormal matrix whose columns are the n input singular vectors. The pseudoinverse is computed as $\lfloor A \rfloor^{-1} = U\Sigma^{-1} V^T$, where $\Sigma^{-1}$ is an n×6 matrix, where the upper-most 6×6 elements form a diagonal matrix with the $j^{th}$ diagonal element defined as $1/\sigma_j$ if $\sigma_j \neq 0$ and as 0 if $\sigma_j = 0$, and all other entries equal 0, see Horn et al. The sixth singular value will always be $\sigma_6 = 0$ and the sixth column of U will always be $$U_6 = [0\ 0\ 1\ 0\ 0\ 0]^T \quad (11)$$

corresponding to torque generation about the magnetization axis, which is never possible. It is required that the other five singular values are nonzero for full 5-DOF control.

In the case of a microrobot moving through fluid, where the microrobot can align with the applied field unimpeded, and a modified control strategy can be used. Rather than explicitly controlling the torque, the magnetic field can be controlled to the desired orientation, to which the microrobot will naturally align, and then the force on the microrobot is controlled explicitly:

$$\begin{bmatrix} B \\ T \end{bmatrix} = \begin{bmatrix} \lfloor B(P) \rfloor \\ M^T \lfloor B_x(P) \rfloor \\ M^T \lfloor B_y(P) \rfloor \\ M^T \lfloor B_z(P) \rfloor \end{bmatrix} \begin{bmatrix} i_1 \\ \vdots \\ i_n \end{bmatrix} = \lfloor A_{B,F}(M, P) \rfloor I \quad (12)$$

Then the currents I is set as $$I = \lfloor A_{B,F}(M, P) \rfloor^{-1} \begin{bmatrix} B_{des} \\ F_{des} \end{bmatrix} \quad (13)$$

Full 5-DOF control, which required a rank-5 actuation matrix in (9), corresponds to a rank-6 actuation matrix in (12). As with (9), the use of (12) requires knowledge of the microrobot's pose and magnetic moment. However, in this case the microrobot will align with the applied field under open-loop control. If it is ensured that the direction of B does not change too rapidly, it is reasonable to assume that M is always aligned with B, which means that there is no need to measure the microrobot's full pose explicitly, but rather, the magnitude of M is to be estimated and the microrobot's position P is to be measured. In addition, if a magnetic field should be generated that does not vary greatly across the workspace, so that it is reasonable to assume that the microrobot is always located at P=0 for purposes of control, eliminating the need for any localization of the microrobot.

There are a number of potential methods to generate the unit-current field maps that are required for the proposed control system. Either the magnetic field of the final system can be explicitly measured at a grid of points or the field values can be computed at the grid of points using FEM models. In either case, trilinear interpolation is used during real-time control. For each of the electromagnets, a unit-current field map has to be calculated, but it is possible to calculate fewer maps, and then rotate them during run time using homogeneous transformations. Potentially electromagnets of different geometry and size at different distances from the centre could be used which would require the calculation of the unit-current field map for each of the electromagnets individually. To generate the unit-current gradient maps using either method, either the gradient is explicitly measured/modeled at the grid of points, or the field data is numerically differentiated, so care must be taken to minimize noise in the field map. An alternative to the trilinear-interpolation approach is to fit a continuous function to the field. This is the approach that is used here. The analytical field model also has a simple analytical derivative. These analytical models are used to build the unit-current field and gradient maps during run time and are described in more detail in Section V-B.

Throughout the calculation within the embodiment described here, we use a constant $|B|=15$ mT: this value was chosen after preliminary testing because it results in low peak currents in the electromagnets during typical operation. Keeping $|B|$ constant keeps the control-system equations linear and enables (13) to be computed in one iteration, but it is suboptimal. Allowing $|B|$ to vary would result in somewhat better performance, but at the added computation cost of optimization in real time. Of course, it is possible to choose a different constant value of $|B|$, e.g. $|B|$ between 5 mT and 100 mT.

The control system proposed in the description of this embodiment is quite simple, but it overcomes problems of the prior art. Conventional knowledge dictates that developing linear control systems requires air-core electromagnets, whose individual fields linearly superimpose. However, soft-magnetic cores are desirable because they provide an increase in magnetic-field strength compared to air-core electromagnets. Computing the linear contributions of multiple electromagnets that have high-performance soft-magnetic cores in situ is a novel concept which overcomes prior art considerations.

As mentioned above the electromagnets 21 to 24 of the embodiment shown in FIGS. 1 to 4 are also called the lower set while the electromagnets 31 to 34 above the plane of magnets 21 to 24 are called the upper set. Within this preferred embodiment each pair of adjacent electromagnets is spaced with an angle of $\theta=45$ degrees in the plane of the lower set according to FIG. 1, wherein one magnet of the lower set is always adjacent to two magnets of the upper set and vice versa. The magnets 31 to 34 of the upper set are each inclined in an angle of $\Phi=45$ against the plane of the magnets of the lower set 21 to 24. Therefore, in the case of these eight electromagnets, each of the electromagnets of this first group 21-24 having an angular distance of 90 degrees ($2\times\theta$) one from another, wherein the other second group of four electromagnets 31-34 are all inclined in an angle of 45 degree ($\Phi$) against the plane of the first group, each of the electromagnets of this second group (31-34) having an angular distance of 90 degrees ($2\times\theta$) one from another. As shown in the Figs. the electromagnets of the first group 21-24 and the second group 31-34 are regularly spaced at 45 degrees one from another.

In another embodiment, providing less control over the magnetic element, only six electromagnets are provided. There, a first group of three electromagnets is arranged below a plane, all inclined in an angle of 45 degree against said plane, and all having an angular distance of 120 degrees one from another in view of said plane. The other second group of three electromagnets are all inclined in an angle of 45 degree ($\Phi$) against said plane opposite to the first group, each of the electromagnets of this second group having an angular distance of 120 degrees one from another. It is then preferred that the electromagnets of the first group and the second group are regularly spaced at 60 degrees one from another. This means that the longitudinal axis 101 of any of the electromagnets of the second group is also the longitudinal axis 101 of a corresponding electromagnet of the first group, so that they can be considered aligned on the same axis.

In a further additional embodiment (not shown in the drawings) an n=6 arrangement of electromagnets is used, wherein three magnets are in the plane, i.e. the lower set, and three magnets are at 45 degrees, i.e. the upper set, wherein the angles between adjacent electromagnets in a view on the lower set are always 120 degrees.

However, there is nearly an order of magnitude improvement in the worst-case magnetic element pose when the number of electromagnets was increased from six to eight (from 2×3 to 2×4). Probably the most striking feature of the 2×4 configuration according to FIG. 1 is its lack of symmetry. Intuition might lead one to believe that electromagnets must uniformly surround the workspace in order to create an isotropic behaviour, but that is not the case. With the configuration according to FIGS. 1 and 2, any magnetic element in the workspace 3 can be pushed downward as well as pulled upward and sideways, and this can be done while maintaining any microrobot orientation.

The electromagnets 21 to 24 and 31 to 34 according to a prototype built according to FIGS. 1 and 2 consist of a coil 12, that has dimensions $d_{inner}$=44 mm, $d_{outer}$=63.2 mm, and l=210 mm, where $d_{inner}$, $d_{outer}$, and l are inner diameter, outer diameter, and length, respectively. The coil carries N=712 wraps of 16 mm diameter, insulated copper wire that is 6 layers deep. The electromagnet cores 11 are made of VACOFLUX 50, which is a CoFe alloy from VACUUMSCHMELZE. Its saturation magnetization is on the order of 2.3 T, the coercivity is 0.11 mT, and the maximum permeability is 4500 H/m. The core has a diameter of 42 mm and a length of 210 mm. It has an inductance of 89 mH and a resistance of 1.3Ω.

The chosen power supply for the system is a SM 70-90 by Delta Elektronica BV. This supply is capable of providing 6 kW to the system, and enables all eight channels to be driven at 20 A simultaneously. The current for the electromagnetic coils is sourced through switched amplifiers having a switching frequency of 150 kHz, which is well above the frequency that would be perceived in microrobot control. The switched amplifiers are controlled through two Sensoray 626 DAC cards with 14-bit resolution.

In typical operating conditions, the temperature of the coils will rise to approximately 60° C. during a manipulation task. If the operator wishes to apply the maximum force capable for extended periods of time, the system will rapidly heat up in excess of this. To prevent the temperature reaching a critical stage, a cooling system 13 consisting of copper tubing that surrounds each coil is implemented. While running cooling water through the tubing, temperatures have not exceeded 45° C., even with prolonged application of the maximum current the system is capable of exerting.

The system preferably comprises a visualization unit, as exemplified by 44 in FIG. 9, adapted to detect the position of a magnetic element inside the workspace 3. Such a system comprises e.g. two stationary camera assemblies 44 providing visual feedback from the top and side. The cameras 44 are Basler A602f 100 fps monochrome CMOS firewire cameras. The cameras 44 are each fitted with an Edmund Optics VZM 200i 2× zoom lens with a working distance of 90 mm, a depth-of-field of 1.5 mm, and a frame size of 640∴480 pixels. Each camera assembly 44 is mounted on a Thorlabs DT25/M translation stage, which is used for focusing. Position feedback is achieved with visual processing using the OpenCV library. The simplified experimental environment enables successful tracking through the use of adaptive thresholding and morphological operators such as erosion and dilation. The tracking precision is primarily limited by the resolution of the cameras and optics. The entire system is controlled through C++ by a single computer 41 with an Intel Core 2 Duo 2.6 GHz processor running Ubuntu Linux.

Beside the use of a visualization unit 44 it is also contemplated that modalities such as magnetic sensors, computed tomography (CT) x-ray, fluoroscopy or positron emission tomography (PET) (not shown in the drawings) detect the position of the element and provide feedback for the control.

Figure 5:
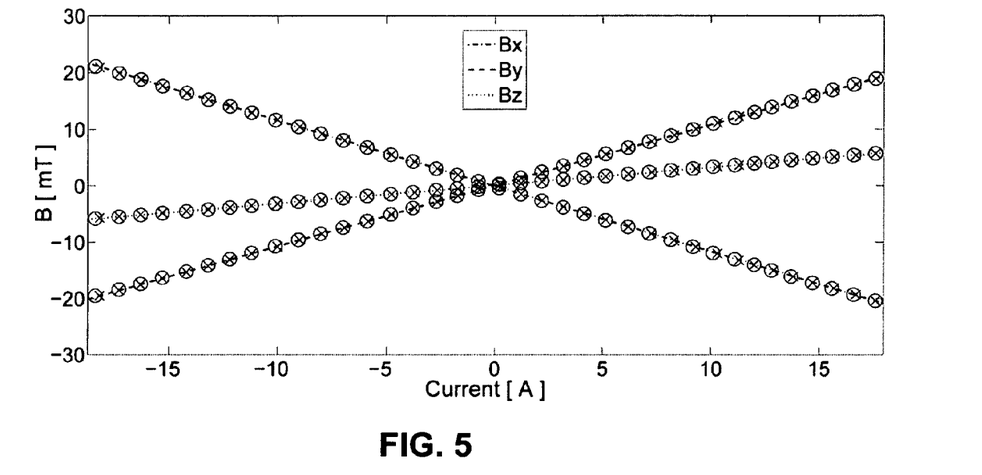
FIG. 5 shows the field measured at the centre of the workspace dependent on the current in a single electromagnet.
Figure 11:
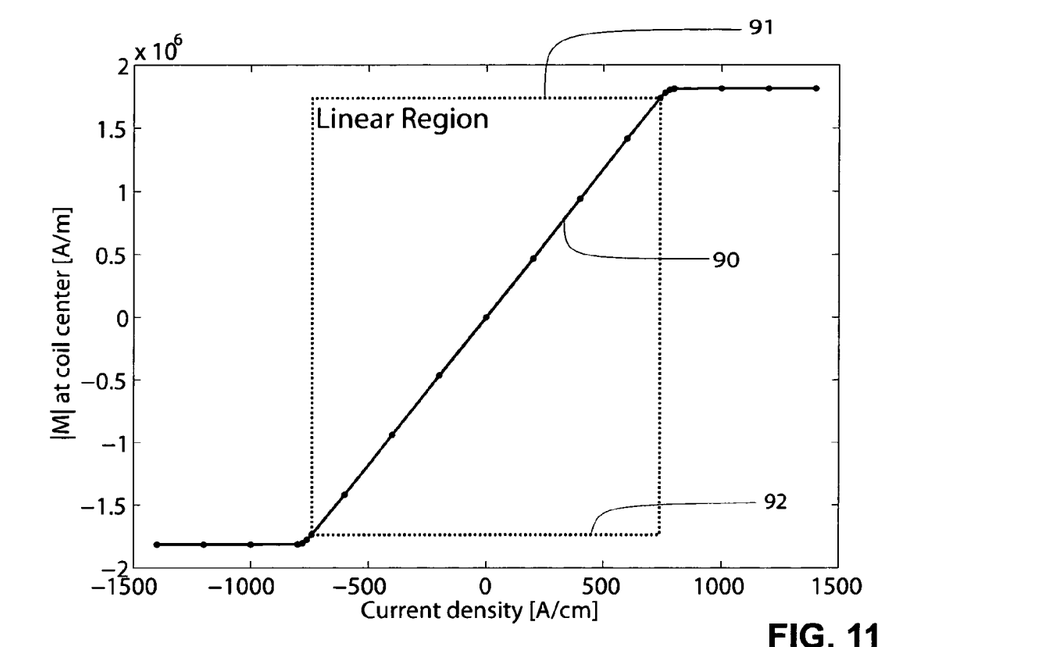
FIG. 11 shows the field measured in the workspace dependent on the current in a single electromagnet similar to FIG. 5 with an indication of the linear region.

The following paragraph relates to a verification of the linearity assumption. The concept design of the invention comprises the assumption that the use of high-performance soft-magnetic material in the cores will result in a system behaviour that is linear with respect to the input currents. In FIG. 5, the field measured at the centre of the workspace 3 is shown dependent on the current in a single electromagnet (Coil 0, i.e. electromagnet 21). The field is measured using a Metrolab THM1176 Three-axis Hall Magnetometer. It was found that (1) there is no perceivable hysteresis below ~18 A, and (2) the "linear" region is very linear. "x" denotes the data for increasing current and "o" denotes the data for decreasing current. It is clear from FIG. 5 that it shows a specific region outside the saturation region of the depicted coils with a current around 0 Ampere. A further explanation of this regime is shown in FIG. 11.

Figure 6:
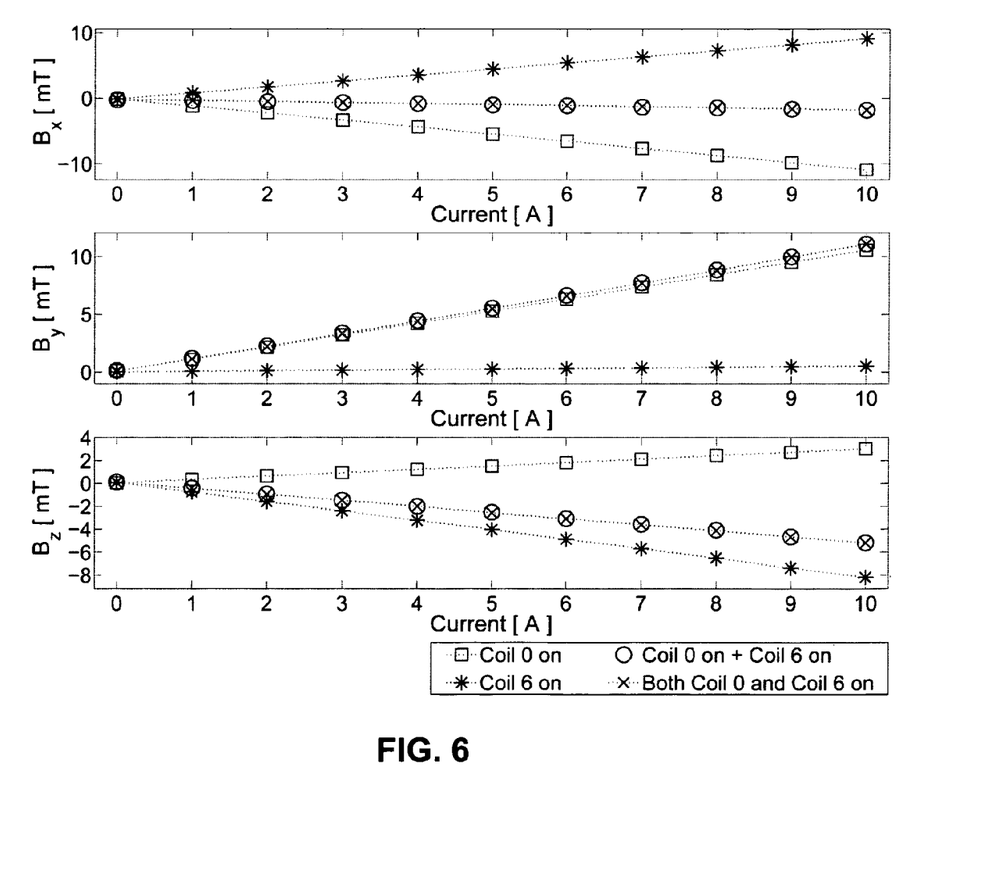
FIG. 6 shows the field measured at the centre of the workspace with a variation of the current in each of two electromagnets.

In FIG. 6, the field measured at the centre of the workspace is shown with a variation of the current in each of two electromagnets (Coil 0, i.e. electromagnet 21 and Coil 6, i.e. electromagnet 33) individually, and then simultaneously. It can be seen from the graph that the field generated by both coils is indeed the sum of the fields generated by the individual coils.

Figure 7:
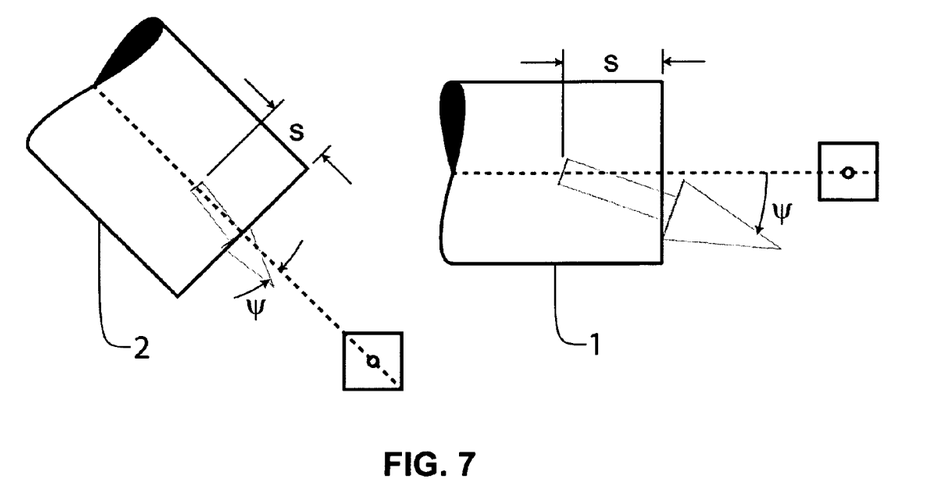
FIG. 7 shows an upper and a lower electromagnet according to an embodiment of the invention.

FIG. 7 shows an upper 2 and a lower 1 electromagnet within a typical configuration. The upper magnet 2 in situ can be modelled as a point dipole with dipole strength Γ=4.51 $Am^2$, location adjustment s=22.5 mm and Ψ=7.6°. The lower magnet 1 in situ can be modelled as a point dipole with Γ=8.178 $Am^2$, s=34.6 mm and Ψ=19.5°. The deviation values Ψ correspond to the representation of the deviation between 101 and 103 in FIGS. 3 and 4.

Figure 8:
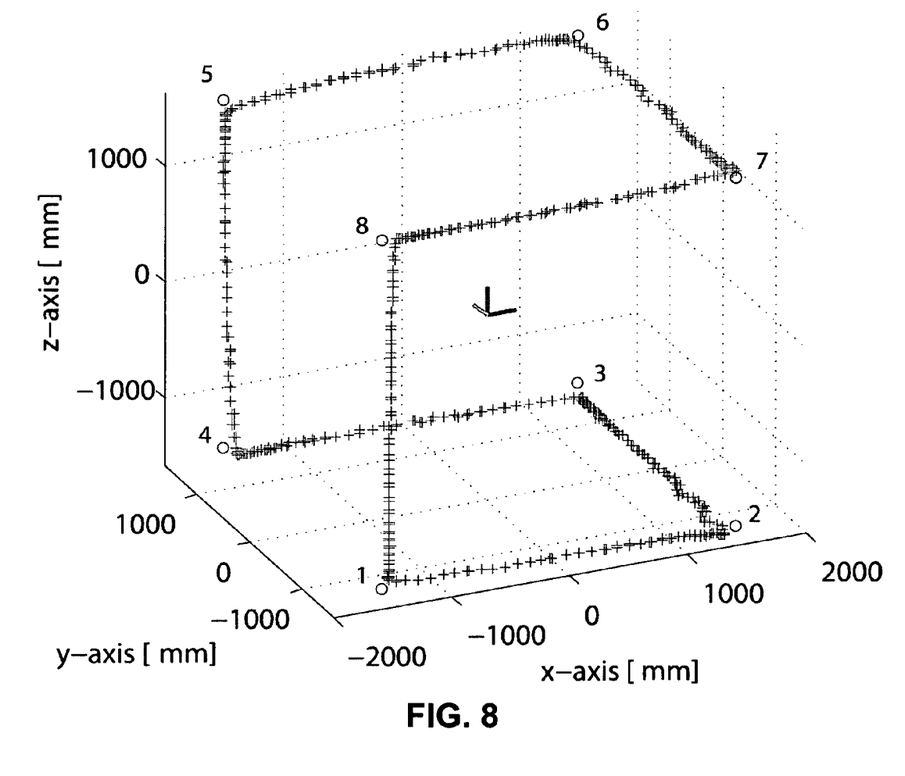
FIG. 8 shows a graph of automated position control.

FIG. 8 shows a graph of automated position control. The microrobot or magnetic element was built according to K. B. Yesin et al. "Modeling and control of untethered biomicrorobots in a fluidic environment using electromagnetic fields" in Int. J. Robotics Research, Vol. 25 no. 5-6, pp. 527-536, 2006. The crosses show waypoints and thus the path of a 2 mm long magnetic element moved along the edges of a cube, between eight points denoted by the "o"'s and spaced at ±1500 μm from the center of the workspace.

The closed loop control was handled by a PD-controller with tracked position from the two cameras 44 mentioned above, since the magnetic element can be moved from one location to another in a holonomic fashion. The magnetic element had been visually servoed to a location in the centre of the workspace 3 and over a series of 400 frames recorded at 30 Hz, the position of the element as returned by the tracker had standard deviations of 6.313, 4.757 and 8.951 μm along the x-, y- and z-axis, respectively, and a maximum distance of 29.77 μm.

Said electromagnets 21 to 24 and 31 to 34 are connected to a control unit 40 consisting of a computer 41, amplifiers 42, and power supply 43 as shown in FIG. 9 supplying the current to the coils 12 of the electromagnets. The amplifiers 42 comprise preferably one amplifier for each electromagnet. These amplifiers are connected with the corresponding electromagnet with a supply line 51. At least one camera 44, preferably two cameras, is/are positioned to acquire an image of the magnetic element in the body 9. The corresponding signals are transmitted with the optic signal connection 52 to the computer 41 of the control unit 40. The computer 41 generates control signals for each amplifier which are transmitted with the control connection 54 to the amplifier unit 42 which is connected with the power supply 43 using a power supply connection 53 and with the computer 41 with an additional status connection 55 to allow the control unit 40 to take into the control any changes in the amplifier regime.

Figure 10:
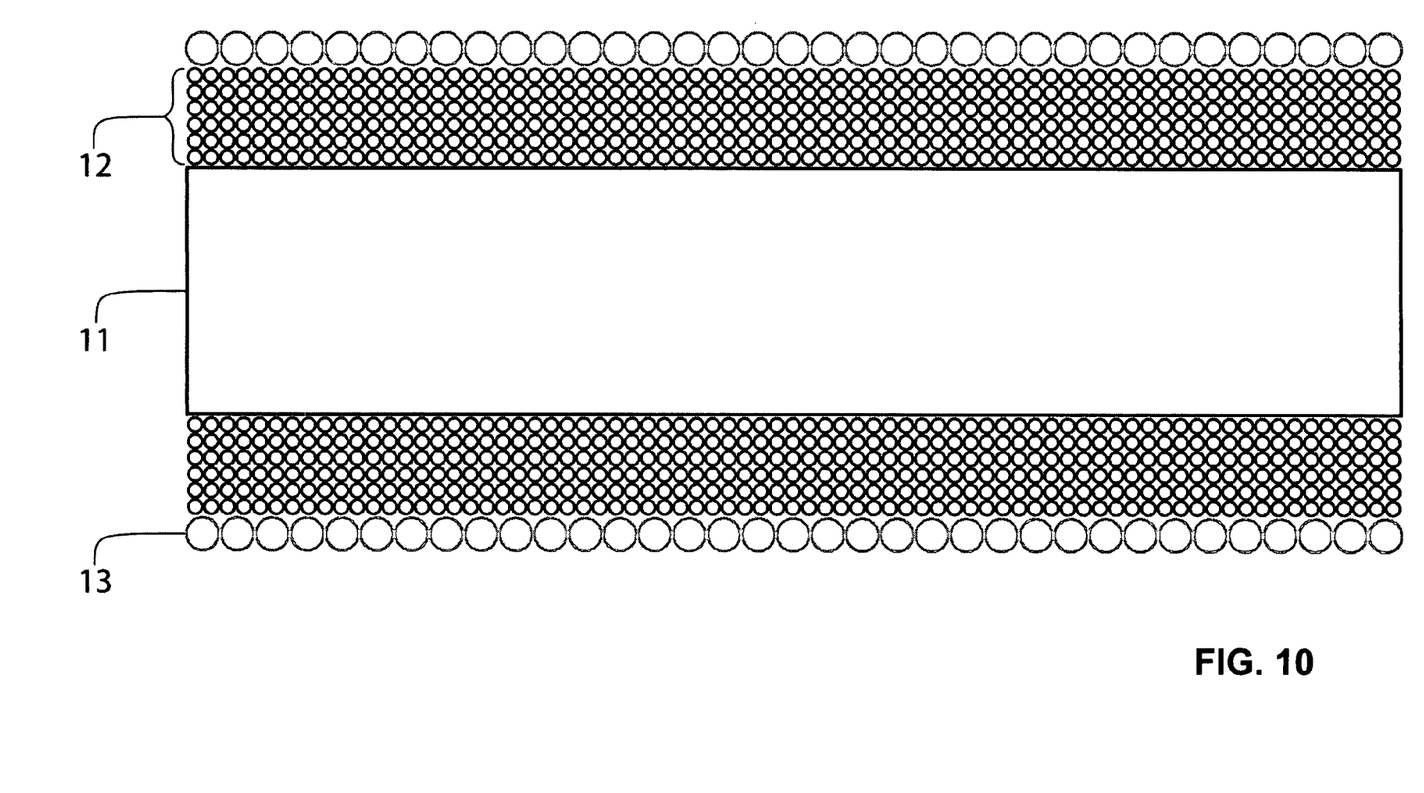
FIG. 10 shows a schematic representation of one electromagnet.

FIG. 10 shows a schematic cross section of an electromagnet as used in the embodiments shown in FIGS. 1 to 9 comprising a core 11, a solenoid 12 and cooling 13. The electromagnet as shown in FIG. 9 has preferably a cylindrical core, but other core forms, such as square cores instead of cylindrical ones can be used.

In order to achieve the control as shown in FIG. 8 or to allow an open loop positioning of the magnetic element/microrobot, the device is undergoing a calibration method as explained above. Every single one of the plurality of electromagnets is supplied (one after the other) with a specific current and the effect in situ in a predetermined space (i.e. the body) is determined. This determination can be a calculation or a measurement. In the case of the embodiments in this specification, it is sufficient to determine the magnetic field for one of the electromagnets, e.g. 21, of the lower set and for one of the electromagnets, e.g. 31, of the upper set. Then the influence of the same supply current of one of the other electromagnets of the same set can be calculated.

Therefore the impact of a supply of said current to all electromagnets can be determined. The resulting magnetic field is predetermined and adapted to maintain the intended magnetic element in place, e.g. levitating in the body. In other words, the supply current and the resulting magnetic field is predetermined based on the kind of microrobot, weight, body consistence, relative distances etc. Said determination can be achieved for single points within said body or it can be assumed that the magnetic field is identical over the whole body space, within which the magnetic element is intended to be controlled. The actual control (as e.g. seen in FIG. 8) with a device according to FIG. 9 is achieved in the linear region around the specific chosen current supply as shown in FIGS. 5 and 6. Therefore, the control is achieved based on the calculation of the linear contributions of multiple electromagnets having high-performance soft-magnetic cores in situ.

FIG. 11 shows the field measured in the workspace dependent on the current in a single electromagnet similar to FIG. 5 with an indication of the linear region 90. The system according to the invention comprises linear regions of the electromagnets 21-24; 31-34, 61-63, 71-72 being delimited by the value of the flux density of each electromagnet being in an interval between e.g. of the 90% negative and positive saturation value of each electromagnet. The linear region is thus defined by the upper 91 and lower 92 threshold values based on the flux density value. The threshold can be fixed at e.g. 70, 80 or 90% of said value being dependent on the interaction of the combined magnets; their configuration and orientation. It is important that the linear region as shown in FIGS. 5 and 11 is not only respected for a single magnet, but also by the single magnets when the whole device receives a control current to provide a specific magnetic regime at the workspace 3 and/or to control an element at said workspace 3.

Figure 12:
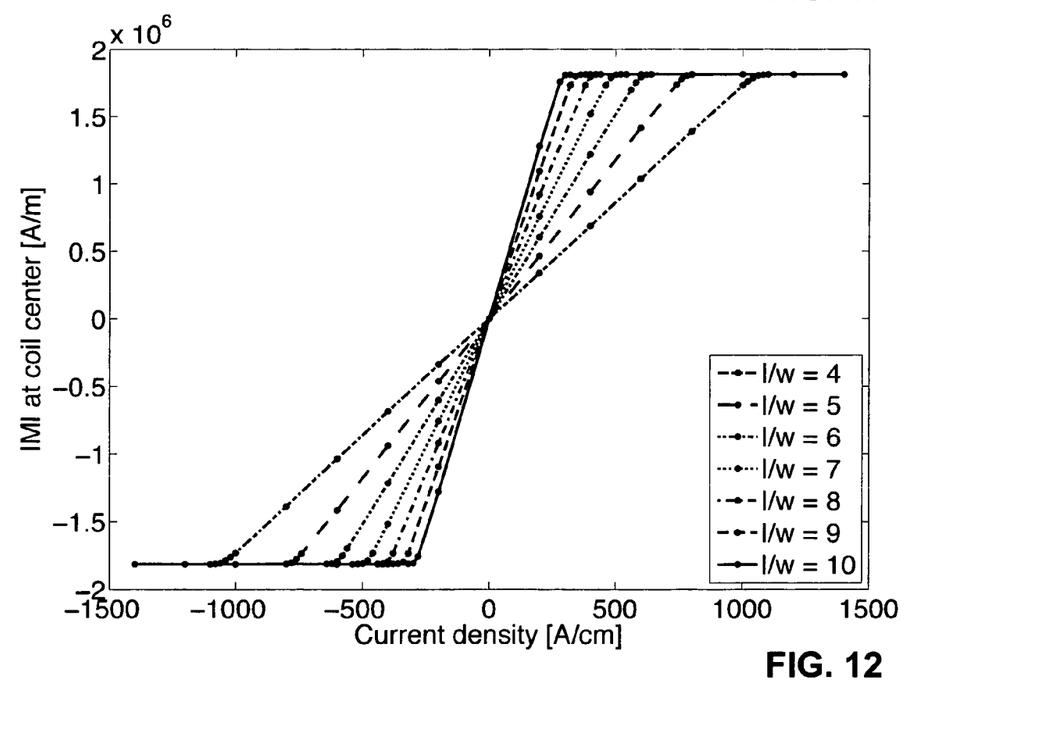
FIG. 12 shows the field measured in the workspace dependent on the current as function of the aspect ratio of the single electromagnets.

FIG. 12 shows the field measured in the workspace 3 dependent on the current as function of the aspect ratio of the single electromagnets for values of this aspect ratio between 4 and 10 (l/w). Therefore the current value has to be smaller for an l/w=10 than for an l/w=4 for identical materials and positions.

Figure 13:
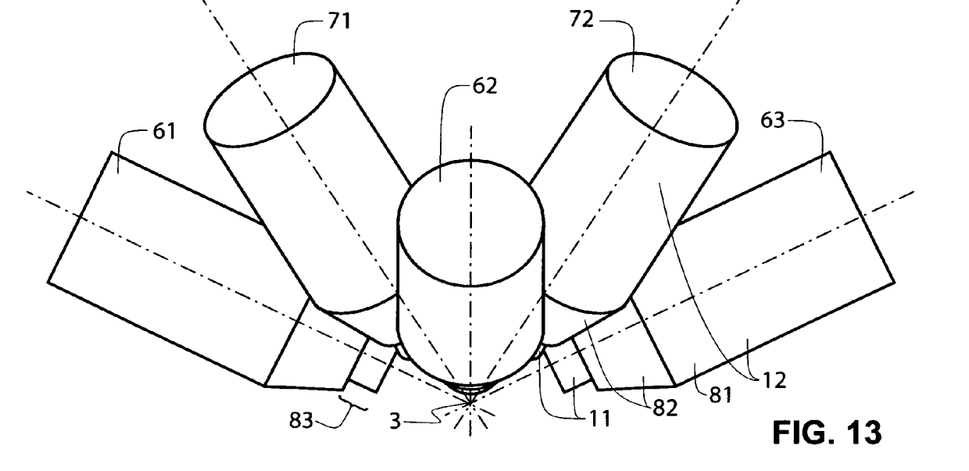
FIG. 13 shows a schematic side-view on the magnets of a system according to another embodiment of the invention.

FIG. 13 shows a schematic side-view on the magnets of a system according to another embodiment of the invention. There are three out of four electromagnets 61, 62, 63 visible from the group of first inclined oriented magnets of about 30 degrees, which are arranged in an angular distance of 90 degrees relating to the perpendicular symmetry axis. Two out of four electromagnets 71, 72 are visible from the group of further inclined oriented magnets, wherein the inclination is more pronounced, e.g. about 45 degrees. The electromagnets 71 and 72 (as well as the magnets not visible in FIG. 13) are also arranged in an angular distance of 90 degrees relating to the perpendicular symmetry axis. Each of the magnets 71, 72 is positioned between two of the first mentioned magnets. The control schemes as mentioned above also apply to this configuration.

One further difference to the embodiment of FIGS. 1 and 2 is the structure of the single magnets. The core 11 of each magnet is positioned nearer to the central workspace 3 of the device, since the enveloping coils 12 and the cooling system (not shown) are arranged as follows. Beside the cylindrical coil arrangement 81 known from FIG. 1, there is a tapered coil arrangement 82 ending at a specific distance from the naked core. The naked core part 83 can have a length of about the radius of the core 11 itself Then the tapered coil arrangement 82 provides a growing number of coils around the core, until the usual cylindrical arrangement 81 making 66 to 80 percent of the length of the magnet is reached. This arrangement allows a more confined workspace 3, since the isolated tapered coil arrangement 82 is not hindering the arrangement of adjacent magnets 61-71-62-72-63 as shown in FIG. 13, since these arrangements 82 and 83 take less space than the magnets according to the embodiment shown in FIG. 1. The aspect ratio width to length of the cores of magnets 61, 62 etc. is 1:5. Preferred aspect ratios are between 1:4 to 1:10 according to the invention.

The invention claimed is:

1. A magnetic manipulation and navigation system for moving a magnetic element through a body comprising at least six electromagnets fixed in relation to said body and a control unit supplying the current for the electromagnets, wherein the electromagnets have soft magnetic cores, and wherein the current supplied by the control unit to each of the electromagnets is adapted to operate the electromagnetic coils of each of the electromagnets in their cores' linear regions, wherein the linear regions of the electromagnets are delimited by the value of the flux density of each electromagnet being in an interval between the negative and positive saturation value of each electromagnet.

2. The system according to claim 1, wherein the delimitation of the linear regions of the electromagnets is set to be the 70%, 80% or 90% threshold value of the negative and positive saturation value of each electromagnet.

3. The system according to claim 1, wherein the soft magnetic cores of the electromagnets have a saturation magnetisation on the order of 1 T and a coercivity below 1000 A/m.

4. The system according to claim 3, wherein the soft magnetic cores of the electromagnets have a saturation magnetisation of more than 2 T and a coercivity below 300 A/m.

5. The system according to claim 1, wherein the aspect ratio of width to length of each electro magnet is 4 or higher.

6. The system according to claim 1, wherein the aspect ratio of width to length of each electro magnet is between 4 and 10.

7. A magnetic manipulation and navigation system for moving magnetic element through a body comprising at least six electromagnets fixed in relation to said body and a control unit supplying the current for the electromagnets, wherein the electromagnets have soft magnetic cores, and wherein the current supplied by the control unit to each of the electromagnets is adapted to operate the electromagnetic coils of each of the electromagnets in their cores' linear regions, wherein the control unit comprises a calculation module adapted to calculate the desired current through each of the coils by building a linear set of equations that describe the torque and force, or alternately the field orientation and force, resulting from the current through the coils.

8. The system according to claim 7, wherein the calculation module comprises a pseudoinverse or equivalent least squares solution of the linear set of equations to calculate the desired current in each of the electromagnets for a given desired torque and force, or alternately for a given desired field orientation and force.

9. A magnetic manipulation and navigation system for moving a magnetic element through a body comprising at least six electromagnets fixed in relation to said body and a control unit supplying the current for the electromagnets, wherein the electromagnets have soft magnetic cores, and wherein the current supplied by the control unit to each of the electromagnets is adapted to operate the electromagnetic coils of each of the electromagnets in their cores' linear regions, wherein the control unit is connected to a visualization unit, adapted to detect the position and/or orientation of a magnetic element inside the workspace.

10. The system according to claim 9, wherein the output signal of said visualization unit is connected to a closed-loop module of the control unit.

11. The system according to claim 1, wherein, in the case of eight electromagnets, a first group of four electromagnets is arranged approximately in a plane, each of the electromagnets of this first group having an angular distance of between 80 to 100 degrees one from another, wherein the other second group of four electromagnets are all inclined in an angle of between 35 to 55 degrees against the plane of the first group, each of the electromagnets of this second group having an angular distance of between 80 to 100 degrees one from another, wherein the electromagnets of the first group and the second group are regularly spaced at between 35 to 55 degrees one from another.

12. The system according to claim 11, wherein, each of the electromagnets of this first group having an angular distance of 90 degrees one from another, wherein the other second group of four electromagnets are all inclined in an angle of 45 degrees against the plane of the first group, each of the electromagnets of this second group having an angular distance of 90 degrees one from another, wherein the electromagnets of the first group and the second group are regularly spaced at 45 degrees one from another.

13. The system according to claim 1, wherein, in the case of six electromagnets, a first group of three electromagnets is arranged approximately in a plane, each of the electromagnets of this first group having an angular distance of between 110 to 130 degrees one from another, wherein the other second group of three electromagnets are all inclined in an angle of between 35 to 55 degrees against the plane of the first group, each of the electromagnets of this second group having an angular distance of between 110 to 130 degrees one from another, wherein the electromagnets of the first group and the second group are regularly spaced at between 50 to 70 degrees one from another.

14. The system according to claim 1, wherein, in the case of six electromagnets, a first group of three electromagnets is arranged below a plane, all inclined in an angle of between 35 to 55 degrees against said plane, and all having an angular distance of between 110 to 130 degrees one from another in view of said plane, wherein the other second group of three electromagnets are all inclined in an angle of between 35 to 55 degrees against said plane opposite to the first group, each of the electromagnets of this second group having an angular distance of between 110 to 130 degrees one from another, wherein the electromagnets of the first group and the second group are regularly spaced at between 50 to 70 degrees one from another.

15. The system according to claim 1, wherein, in the case of eight electromagnets, a first group of four electromagnets is arranged above a plane, all inclined in an angle of between 20 to 40 degrees against said plane, and all having an angular distance of between 80 to 100 degrees one from another in view of said plane, wherein the other second group of four electromagnets are arranged above said plane, all inclined in an angle of between 35 to 55 degrees against said plane, each of the electromagnets of this second group having an angular distance of between 80 to 100 degrees one from another, wherein the electromagnets of the first group and the second group are regularly spaced at between 40 to 50 degrees one from another.

16. The system according to claim 1, wherein the control unit is adapted to provide a calibration method, within which every single one of the plurality of electromagnets is supplied one after the other with a predetermined current and the effect in situ in said body is determined; wherein the resulting magnetic field within said body upon supply of said predetermined current to all electromagnets is determined, wherein the control unit generates control signals for the electromagnets in the linear region around said predetermined current.

17. The system according to claim 1, wherein only one of the plurality of electromagnets of the first group and one of the plurality of electromagnets of the second group are supplied with said predetermined current before the resulting magnetic field is calculated for all electromagnets.

18. The system according to claim 1, wherein a portion of the cores of the electromagnets directed towards the workspace is naked, preferably for a length equivalent to the radius of the core, followed by a broadening coil arrangement until a cylindrical coil arrangement encompassing the remainder of the core.

* * * * *